United States Patent
Laurensou

(10) Patent No.: US 10,500,301 B2
(45) Date of Patent: *Dec. 10, 2019

(54) AGENT FOR SALTING OUT ACTIVE PRINCIPLES IN DRESSINGS CONTAINING AT LEAST ONE OF FATTY SUBSTANCE

(75) Inventor: Christelle Laurensou, Dijon (FR)

(73) Assignee: URGO RECHERCHE INNOVATION ET DEVELOPPEMENT, Chenove (FR)

( * ) Notice: Subject to any disclaimer, the term of this patent is extended or adjusted under 35 U.S.C. 154(b) by 789 days.

This patent is subject to a terminal disclaimer.

(21) Appl. No.: 12/601,718

(22) PCT Filed: May 23, 2008

(86) PCT No.: PCT/FR2008/050893
§ 371 (c)(1),
(2), (4) Date: Jul. 6, 2010

(87) PCT Pub. No.: WO2008/149036
PCT Pub. Date: Dec. 11, 2008

(65) Prior Publication Data
US 2010/0285129 A1    Nov. 11, 2010

(30) Foreign Application Priority Data
May 25, 2007    (FR) ..................................... 07 55272

(51) Int. Cl.
*A61L 15/46*    (2006.01)
(52) U.S. Cl.
CPC .................................. *A61L 15/46* (2013.01)

(58) Field of Classification Search
None
See application file for complete search history.

(56) References Cited

U.S. PATENT DOCUMENTS

| 2,446,793 | A | * | 8/1948 | Shelton et al. | ............... 514/315 |
| 3,929,741 | A | * | 12/1975 | Laskey | ......................... 523/106 |
| 4,231,369 | A | | 11/1980 | Sorensen et al. | |
| 4,367,732 | A | | 1/1983 | Poulsen et al. | |
| 4,912,093 | A | * | 3/1990 | Michaeli | ........................ 514/53 |

(Continued)

FOREIGN PATENT DOCUMENTS

| EP | 264299 | 4/1988 |
| EP | 272149 | 6/1988 |

(Continued)

OTHER PUBLICATIONS

D. W. Brett: "A review of moisture-control dressings in wound care"; J Wound Ostomy Continence Nurs., Nov./Dec. 2006, pp. 3-8.

(Continued)

*Primary Examiner* — Isis A Ghali
(74) *Attorney, Agent, or Firm* — Hamre, Schumann, Mueller & Larson, P.C.

(57) ABSTRACT

The present invention relates to the use, as an agent for salting out an active substance in a composition for a dressing, of a copolymer of a salt of 2-methyl-2-[(1-oxo-2-propenyl)amino]-1-propanesulphonic acid and the 2-hydroxyethyl ester of propenoic acid. It also relates to dressings of the type comprising at least one fatty substance and/or an elastomeric matrix and at least one active substance, which incorporate the aforementioned copolymer.

23 Claims, 1 Drawing Sheet

(56) References Cited

U.S. PATENT DOCUMENTS

| | | | | |
|---|---|---|---|---|
| 5,681,579 | A | * | 10/1997 | Freeman ................. 424/448 |
| 5,968,001 | A | | 10/1999 | Freeman |
| 6,051,748 | A | | 4/2000 | Auguste et al. |
| 6,197,287 | B1 | * | 3/2001 | Mallo et al. ............ 424/70.16 |
| 6,375,977 | B1 | * | 4/2002 | Auguste et al. ............ 424/447 |
| 6,794,555 | B2 | | 9/2004 | Apert et al. |
| 2002/0197302 | A1 | * | 12/2002 | Cochrum et al. ............ 424/445 |
| 2004/0043135 | A1 | | 3/2004 | Han et al. |
| 2004/0241215 | A1 | * | 12/2004 | Lipman ................. 424/445 |
| 2006/0018852 | A1 | | 1/2006 | Fares et al. |
| 2007/0292375 | A1 | * | 12/2007 | Woehrmann et al. ......... 424/68 |
| 2010/0204174 | A1 | | 8/2010 | Laurenson |

FOREIGN PATENT DOCUMENTS

| | | |
|---|---|---|
| EP | 1272229 | 1/2003 |
| FR | 2 392 076 | 12/1978 |
| FR | 2 495 473 | 6/1982 |
| FR | 2 782 086 A | 2/2000 |
| JP | 2006-342098 | 12/2006 |
| WO | 98/10801 | 3/1998 |
| WO | 00/16723 | 3/2000 |
| WO | WO 00/14131 | 3/2000 |
| WO | 01/070285 | 9/2001 |
| WO | WO 01/70285 A1 | 9/2001 |
| WO | 2006007844 | 1/2006 |

OTHER PUBLICATIONS

Hehenberger et al.: "Inhibited proliferation of fibroblasts derived from chronic diabetic wounds and normal dermal fibroblasts treated with high glucose is associated with increased formation of I-lactate"; online abstract, www.ncbi.nlm.nih.gov/pubmed/9776856, 1998, vol. 6(2), 1 page.

English translation of Korean Office Action issued in Korean Application No. 10-2009-7023178, dated Feb. 26, 2015.

West, Jennifer: "Polymers for the management of wound healing"; Trends in Polymer Science, Elsevier Science Publishers, vol. 4, No. 7, Jul. 1996, pp. 206-207.

Chakravarthy, D., "Advances in Pressure Sensitive Adhesive Technology", in "Wound Dressings" edited by Donatas Satas, 1994, pp. 158-171.

"Handbook of Pressure Sensitive Technology", edited by Donatas Satas $3^{rd}$ ed. Satas & Associates, Warwick, Rhode Island, 1999.

Seppic: Sepinov™ EMT 10 (Online) Apr. 2005, pp. 1-31, XP002463431.

Boateng et al.: "Wound Healing Dressings and Drug Delivery Systems: A Review"; Journal of Pharmaceutical Sciences, vol. 97, No. 8, 2008, pp. 2892-2923.

Martin et al.: "Cellular and Molecular mechanisms of repair in acute and chronic wound healing"; British Journal of Dermatology, vol. 173, 2015, pp. 370-378.

Monaco et al.: "Acute wound healing, An Overview"; Clinics in Plastic Surgery, 2003, vol. 30, pp. 1-12.

* cited by examiner

|  | 48h | 96h | 168h |
|---|---|---|---|
| Control | 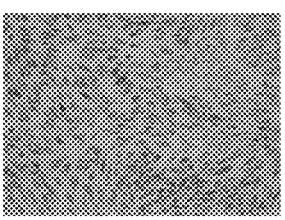 | 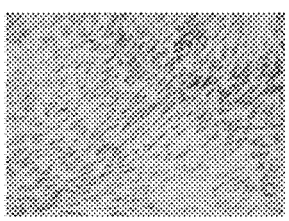 | 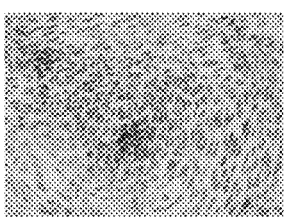 |
| Example 1 | 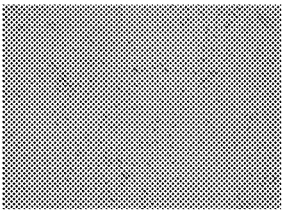 | 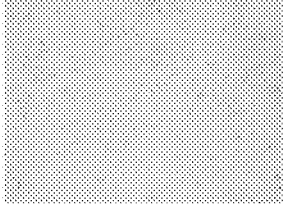 | 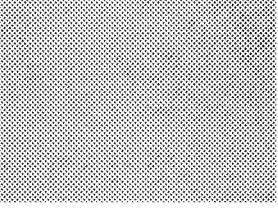 |
| Example 23 | 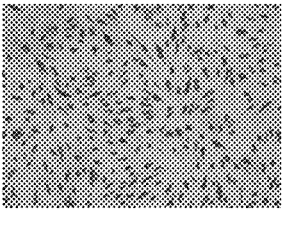 | 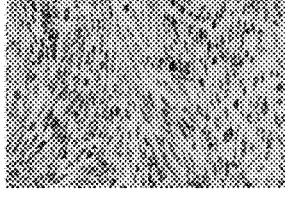 | 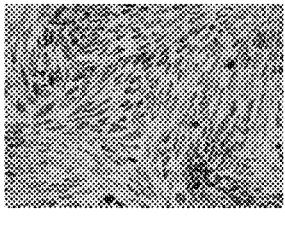 |

AGENT FOR SALTING OUT ACTIVE PRINCIPLES IN DRESSINGS CONTAINING AT LEAST ONE OF FATTY SUBSTANCE

Many dressings which use compositions consisting of fatty substances, generally based on oil or on petroleum jelly, and/or of an elastomeric matrix, into which more or less large amounts of hydrocolloid particles can be incorporated, are today used for treating wounds.

Thus, by way of examples, mention may be made of the products sold under the names Tulle Gras® by the company Solvay Pharma, Physiotulle® and Comfeel® by the company Coloplast, and Urgotul®, Algoplaque® and Cellosorb® by Laboratoires Urgo.

The compositions used in these dressings are generally designed so as not to adhere to the wound and to promote healing by creating a moist environment at the wound.

In order to enable absorption of the exudates from the wound, these compositions may contain large amounts of hydrocolloids, for instance in the products Algoplaque® sold by Laboratoires Urgo and Comfeel® sold by Coloplast, or may be incorporated into dressings associated with one or more absorbent compresses, for instance in the products Tulle Gras®, Physiotulle® and Urgotul®, or complexed with an absorbent foam as in the product Cellosorb®.

These compositions may also be designed so as to allow the dressings incorporating them to be held in place without the aid of an additional adhesive strip, by adhering to the skin.

Compositions for dressings incorporating various active substances intended to be released in order to act in the wound bed or around the edges of the wound in the region generally known as the perilesional skin, have also been designed.

By way of examples of such active substances, mention may thus be made of antiseptic or antibacterial compounds such as silver salts; compounds which act on the healing process, such as antiproteases, or else compounds which act to relieve pain, such as nonsteroidal anti-inflammatories.

Dressings prepared using compositions containing an active substance are, for example, sold by the company Laboratoires Urgo under the names Urgotul® SAg or Cellosorb® Ag.

However, the incorporation of an active substance into these compositions based on a fatty substance and/or on an elastomeric matrix is a complex problem.

The hydrophobic nature of these compositions makes it difficult to incorporate hydrophilic active substances therein.

In addition, the active substance is generally released in the immediate vicinity of the wound exudates. As a result, depending on its solubility in hydrophilic media, the active substance has a more or less marked tendency to remain trapped in the composition and, consequently, to be available. It may therefore be necessary to incorporate large amounts of active substance when the latter has a tendency to remain trapped in the composition.

Moreover, the addition of an active substance to a dressing composition should be done by preserving the properties of cohesion or of absorption (or even of adhesion, when the dressing adheres to the skin), which are always difficult to obtain, in particular in the case of compositions which contain large amounts of hydrocolloids.

The addition of an active substance to a dressing composition should also be done while avoiding the possible problems of interaction between said substance and the constituents of the composition.

In order to remedy these problems, it has been proposed, in patent application No. EP 272 149, to incorporate the into the hydrocolloid which, when swollen following absorption of the exudates, allows the release of said active substance.

This solution, in addition to the fact that it is complex to implement, is not suitable for compositions which contain only small amounts of hydrocolloids and, a fortiori, for compositions which do not contain hydrocolloids. For such compositions, it has been proposed, in patent EP 1 272 229, to incorporate a surfactant, and in particular the product sold under the name Montanox® 80, into the composition in order to promote the release of the active substance i.e. in this particular case an antibacterial substance such as a silver salt.

However, the presence of a surfactant in a dressing composition raises another problem. Indeed, owing to their amphiphilic character, surfactant compounds are known to act on the cell walls and result in the lysis thereof.

In the context of the healing process where it is desired to heal the wound, it is sought, in particular during the granulation phase, to induce or accelerate cell proliferation and more specifically the proliferation of fibroblasts, which are the essential cells of this phase and which will result in the reconstruction of the connective tissue that makes it possible to heal the wound. However, the surfactants and in particular Montanox® 80 described in this prior art patent are toxic to fibroblasts.

Under these circumstances, it would therefore be desirable to have a releasing agent which is not a surfactant so as not to interfere with cell proliferation during this healing process, or even more favorably to promote this cell proliferation.

It would also be desirable for this releasing agent to be able to act at concentrations in the region of those of a surfactant in order to prevent complete (qualitative and quantitative) reformulation of the composition.

An object of the present invention is to solve the technical problem consisting of the provision of a novel agent for releasing an active substance, which is not toxic to cells, in particular fibroblasts, and which can be readily incorporated into the compositions for a dressing based on a fatty substance and/or on an elastomeric matrix, in the presence or absence of hydrocolloids, without impairing the cohesion, absorption or adhesion properties of said compositions, regardless of the solubility of the active substance with respect to liquids and in particular with respect to the exudates of the wound.

It has been discovered, and this constitutes the basis for the present invention, that it is possible to solve this technical problem in a particularly simple manner that can be used on an industrial scale by using, as agent for releasing an active substance, a copolymer of a salt of 2-methyl-2-[(1-oxo-2-propenyl)amino]-1-propanesulfonic acid and of 2-hydroxyethylpropenoate ester.

The expression "salt of 2-methyl-2-[(1-oxo-2-propenyl)amino]-1-propanesulfonic acid" is intended to mean herein salts of any type known to those skilled in the art, such as sodium salts, potassium salts, ammonium salts, etc. In the present invention, the sodium salt of 2-methyl-2-[(1-oxo-2-propenyl)amino]-1-propanesulfonic acid is preferably used.

The abovementioned copolymer is a product known per se, in particular in the cosmetics field, owing to its emulsifying-stabilizing properties and its good thickening capacity. Such a product is, for example, sold by the company Seppic under the trade name Sepinov EMT 10®.

Thus, according to a first aspect, an object of the present invention is the use, as an agent for releasing an active substance in a composition for a dressing, of a copolymer of a salt of 2-methyl-2-[(1-oxo-2-propenyl)amino]-1-propanesulfonic acid and of 2-hydroxyethylpropenoate ester.

This copolymer is particularly advantageous insofar as, when it is incorporated into masses comprising at least one fatty substance and/or one elastomeric matrix, it makes it possible to release various active substances in proportions equivalent to those obtained with a surfactant.

It has, moreover, been discovered that this copolymer, unlike the known surfactant compounds, has a tendency to induce fibroblast proliferation, which constitutes a particularly valuable advantage. More specifically, when the effect of a conventional surfactant, such as polysorbate 80, on healing, more specifically on fibroblasts, is studied, it is seen that said surfactant exhibits toxicity with respect to these cells. On the other hand, it has been observed that a copolymer of a salt of 2-methyl-2-[(1-oxo-2-propenyl)amino]-1-propanesulfonic acid and of 2-hydroxyethylpropenoate ester has a tendency to induce fibroblast proliferation.

According to a second aspect, the present invention relates to a dressing of the type comprising at least one fatty substance and/or one elastomeric matrix and at least one active substance, characterized in that it comprises a copolymer as defined above.

The term "dressing" is intended to cover herein occlusive or nonocclusive dressings.

As nonocclusive dressings, mention may be made of interface dressings, such as those sold under the trade names Tulle Gras® (by Solvay Pharma), Physiotulle® (by Coloplast) or alternatively Urgotul® (by Laboratoires Urgo).

These interface dressings are generally provided in the form of a mesh or of a netting coated with a mass comprising at least one fatty substance and/or one elastomeric matrix.

They may also be constituted of a mass without mesh or netting, having the form of a sheet which may or may not have through-holes, depending on the type of wound to which the dressing is applied (a sheet which has through-holes will preferably be used on an exudative wound when the mass has only a low or no absorbent capacity, the holes thus allowing evacuation of the wound exudates).

These interface dressings may contain one or more active substances. Such dressings containing active substances are, for example, sold under the trade names Urgotul® SAg (by Laboratoires Urgo) containing silver sulfadiazine, and Corticotulle Lumière® (by Solvay Pharma) containing neomycin sulfate and polymyxin B sulfate.

Occlusive dressings are for the most part constituted of several layers, with an internal layer which comes into contact with the wound and an external layer.

These dressings may be in the form of an interface dressing complexed with an absorbent compress, it being possible for said compress to itself be complexed with an adhesive-coated backing. This type of dressing is known, and sold by Laboratoires Urgo under the trade name Cellosorb Ag® (in this case, the interface dressing contains silver sulfate as active substance).

The present invention also finds an application in the preparation of hydrogel-based or hydrocolloid-based dressings into which the abovementioned copolymer is incorporated.

Known hydrocolloid-based dressings are, for example, sold under the names Algoplaque® (by Laboratoires Urgo), Duoderm® (by Convatec) and Comfeel® (by Coloplast). Such dressings are described in the following patent applications: FR 2 392 076, FR 2 495 473 and WO 98/10801, and EP 264 299.

In the context of the present invention, dressings which use compositions constituted of fatty substances and/or of an elastomeric matrix and a hydrocolloid or hydrocolloid particles will be preferred.

The term "hydrocolloid or hydrocolloid particles" is herein intended to mean the compounds used by those skilled in the art for their ability to absorb aqueous liquids such as water, physiological saline solutions or exudates from a wound.

As suitable hydrocolloids, mention may, for example, be made of pectin, alginates, natural plant gums such as, in particular, karaya gum, cellulose derivatives such as carboxymethylcelluloses and their alkali metal salts such as sodium or calcium salts, and synthetic polymers based on acrylic acid salts known as "superabsorbents", for instance the products sold by the company BASF under the name Luquasorb® 1003 or by the company Ciba Specialty Chemicals under the name Salcare® SC91.

These hydrocolloids may be used alone or in combination.

The hydrocolloids that are preferred in the context of the present invention are the alkali metal salts of carboxymethylcellulose, in particular sodium carboxymethylcellulose.

The amount of hydrocolloid incorporated into the polymer matrix will be adjusted according to the desired level of absorption for said mass. Thus, the amount of hydrocolloid may be comprised between about 2% and about 50% by weight, relative to the total weight of the mass.

In the context of the present invention, an amount of hydrocolloid of between 20% and 50% by weight, relative to the total weight of the mass, will preferably be used if it is desired to prepare an absorbent dressing such as those described in FR 2 495 473, FR 2 392 076 or WO 98/10801.

An amount of hydrocolloid of between 2% and 20% by weight, relative to the total weight of the mass, will preferably be used if it is desired to prepare a relatively nonabsorbent dressing such as that described in WO 00/16723.

In the present description, the term "fatty substance" is intended to denote any substance or any mixture of substances chosen from oils, fats and lipid substances (comprising fatty acids, glycerols, sterols and derivatives thereof) of natural (mineral, animal or plant) or synthetic origin and which are in liquid, semi-solid or solid form, it being possible for these substances to be of various molecular weight and structure (monomeric or polymeric).

Among the mineral oils that can be used in the context of the present invention, mention may be made, by way of examples, of paraffin oils, petroleum jelly, and more generally, mineral oils formed from compounds of paraffinic, naphthenic or aromatic nature or from mixtures thereof in varying proportions.

As examples of mineral oils, mention may thus be made of the products sold by the company Shell under the name Ondina® and Risella® for the mixtures based on naphthenic and paraffinic compounds, or under the name Catenex® for the mixtures based on naphthenic, aromatic and paraffinic compounds.

In the context of the present invention, paraffin oils, and in particular the oil sold by the company Shell under the name Ondina® 917, will be preferred.

Plant oils or fats may also be used in the context of the present invention, such as, in particular, groundnut oil, coconut oil, corn oil or sweet almond oil. These plant oils or fats may be hydrogenated or peroxidized.

Animal fats and oils are also suitable, such as in particular tallow oil, lanolin or whale oil.

In the context of the present invention, dressings which use compositions constituted of a fatty substance and of an elastomeric matrix and hydrocolloids or hydrocolloid particles will be preferred.

The term "elastomeric matrix" is herein intended to mean compositions made up of one or more elastomers chosen from poly(styrene-olefin-styrene) block copolymers and one or more compounds chosen from "tackifying" products and plasticizers, preferably liquid plasticizers. Such compositions are thus defined in "Advances in Pressure Sensitive Adhesive Technology" edited by Donatas Satas in April 1995 in chapter 7 "Wound dressings" pages 158 to 171, and are also entirely known to those skilled in the art.

The elastomers of the (styrene-olefin-styrene) block copolymer type that can be used in the context of the present invention are those normally used by those skilled in the art in the preparation of dressings. They may, if necessary, be combined with (styrene-olefin) block copolymers.

These block polymers are therefore either triblock copolymers of the ABA type comprising two styrene thermoplastic end blocks A and a central elastomer block B which is an olefin, or diblock copolymers of the AB type comprising a styrene thermoplastic block A and an elastomer block B which is an olefin. The olefin B blocks of these copolymers may be constituted of unsaturated olefins such as, for example, isoprene or butadiene, or of saturated olefins such as, for example, ethylene-butylene or ethylene-propylene.

In the case of a blend of ABA triblock copolymers and of AB diblock copolymers, commercial blends of ABA triblock copolymers and of AB diblock copolymers that are already available may be used or a blend in any proportion preselected from two independently available products may be prepared.

The products comprising an unsaturated central block are well known to those skilled in the art and are, for example, sold by the company Kraton Polymers under the name Kraton® D. For poly(styrene-isoprene-styrene) copolymers (abbreviated to SIS), mention may also be made of the products sold under the names Kraton® D1107 or Kraton® D1119 BT, and for poly(styrene-butadiene-styrene) copolymers, mention may also be made of the product sold under the name Kraton® D1102. Other poly(styrene-isoprene-styrene) copolymers are also sold by the company Exxon Mobil Chemical under the name Vector®, for example the product sold under the name Vector® 4113.

As examples of commercial blends of ABA triblock and AB diblock copolymers in which B is isoprene, mention may be made of the product sold by the company Exxon Mobil Chemical under the name Vector® 4114 or the product Vector® denoted by the code DPX-565.

All these isoprene-based or butadiene-based copolymers generally have a styrene content of between 10% and 52% by weight relative to the total weight of said copolymer.

In the context of the present invention, poly(styrene-isoprene-styrene) (abbreviated to SIS) triblock block copolymers having a styrene content of between 14% and 30% by weight relative to the weight of said SIS may be used.

Preferably, the product sold by the company Kraton Polymers under the name Kraton® D1111K will be used as poly(styrene-isoprene-styrene) triblock block copolymer and the product Vector® DPX-565 sold by the company Exxon Mobil Chemical will be used as a blend of poly(styrene-isoprene-styrene) triblock block copolymer and of poly(styrene-isoprene) diblock block copolymer.

The products comprising a saturated central block are also well known to those skilled in the art and are, for example, sold by the company Kraton Polymers under the name Kraton® G for poly(styrene-ethylene-butylene-styrene) (abbreviated to SEBS) block copolymers, such as in particular the products Kraton® G1651, Kraton® G1654 or Kraton® G1652, or by the company Kuraray under the name Septon® for poly(styrene-ethylene-propylene-styrene) (abbreviated to SEPS) block copolymers.

As an example of commercial blends of triblock-diblock copolymers, mention may be made of the product sold by the company Kraton Polymers under the name Kraton® G1657, the olefin block of which is ethylene-butylene.

As an example of a particular triblock-diblock blend that can be used in the context of the present invention, mention may be made of the blend of a triblock SEBS such as the product sold by the company Kraton Polymers under the name Kraton® G1651 with a poly(styrene-olefin) diblock material such as poly(styrene-ethylene-propylene) sold by the company Kraton Polymers under the name Kraton® G1702.

In the context of the present invention, the SEBS or SEPS triblock copolymers having a styrene content of between 25% and 45% by weight relative to the weight of said SEBS will be preferred. The products sold by the company Kraton Polymers under the names Kraton® G1651 and Kraton® G1654 will be most particularly preferred.

In general, the thermoplastic elastomer will be used, depending on the nature of the block copolymer, in an amount comprised between about 2% and about 40% by weight, relative to the total weight of the composition.

If necessary, antioxidants may be added to these block copolymers. The term "antioxidants" is herein intended to denote the compounds commonly used by those skilled in the art for providing the stability with respect to oxygen, heat, ozone and ultraviolet radiation of the compounds used in the formulation of hydrocolloid masses, in particular the tackifying resins and the block copolymers. One or more of these antioxidants may be used in combination.

As examples of suitable antioxidants, mention may be made of phenolic antioxidants, such as, in particular, the products sold by the company Ciba Specialty Chemicals under the names Irganox® 1010, Irganox® 565 and Irganox® 1076, and sulfur-containing antioxidants such as, in particular, the zinc dibutyldithiocarbamate sold by the company Akzo under the name Perkacit ZDBC.

These antioxidants may be used in an amount comprised between about 0.05% and about 1% by weight relative to the total weight of the hydrocolloid mass.

In the context of the present invention, the use of Irganox® 1010 will be preferred.

In order to obtain adhesive elastomeric masses, it is also possible to add to these block copolymers "tackifying" products such as those which are normally used by those skilled in the art in the preparation of pressure-sensitive adhesives comprising elastomers, and in particular poly(styrene-olefin-styrene) block copolymers, and in this respect, reference may be made to the prior art document mentioned above or to the handbook by Donatas Satas "Handbook of Pressure Sensitive Technology".

In the context of the present invention, one or more tackifying products may therefore be used in proportions comprised between about 1% and about 70% by weight relative to the total weight of the composition, depending on the other elements of said composition, in order to obtain the adhesive capacity desired for the final composition.

Preferably, a tackifying product or a collection of tackifying products will be used in a proportion of from 10% to 40% by weight, relative to the total weight of the composition.

In general, these tackifying products are chosen from tackifying resins, low-molecular-weight polyisobutylenes and low-molecular-weight polybutenes, or mixtures thereof.

Among the tackifying resins that are suitable according to the invention, mention may be made of modified terpene or polyterpene resins, rosin resins, hydrocarbon-based resins, mixtures of cyclic, aromatic and aliphatic resin, etc., or mixtures of these resins.

Such products are, for example, sold by the company Goodyear under the name Wingtack®, such as in particular the synthetic resin formed from $C_5/C_9$ copolymers, sold under the name Wingtack® 86, or the synthetic polyterpene-based resin sold under the name Wingtack® 10. By way of example, mention may also be made of the resins sold under the name Kristalex® by the company Hercules, such as in particular the alpha-methylstyrene-based resin Kristalex® 3085.

In the context of the present invention, the resins sold by the company Exxon Mobil Chemical under the name Escorez®, and most particularly the synthetic resin sold under the name Escorez® 5380, will be preferred.

As low-molecular-weight polybutenes that can be used as tackifying product for the elastomeric matrix, mention may be made of the products well known to those skilled in the art which are, for example, sold under the name Napvis® by the company BP Chimie.

In the context of the present invention, the product sold under the name Napvis® 10 will be most particularly preferred.

These polybutenes may be used alone or as a blend.

They will preferably be used in proportions comprised between 5% and 30% by weight relative to the total weight of the composition, and more particularly from 8% to 15% by weight.

In the context of the present invention, the term "plasticizer" is intended to mean the plasticizers which are normally used by those skilled in the art for the preparation of pressure-sensitive adhesives comprising thermoplastic elastomers, in particular of the poly(styrene-olefin-styrene) block copolymer type, and which are products that make it possible to improve their stretch, flexibility, extrudability or processability properties, and in this respect, reference may be made to the prior art documents mentioned above.

These plasticizers, which are preferably liquid plasticizers, are compounds that are compatible with the olefin central block of the block copolymers used. As liquid plasticizer, use may be made of plasticizing oils, and in particular mineral oils which are formed from compounds of paraffinic, naphthenic or aromatic nature or from mixtures thereof in varying proportions.

By way of example of mineral oils, mention may thus be made of the products sold by the company Shell under the name Ondina® and Risella® for mixtures based on naphthenic and paraffinic compounds, or under the name Catenex® for mixtures based on naphthenic, aromatic and paraffinic compounds.

In the context of the present invention, paraffin oils, and in particular the oil sold by the company Shell under the name Ondina® 917, will preferably be used.

As liquid plasticizer, it is also possible to use, not a plasticizing oil, but synthetic products based on liquid mixtures of saturated hydrocarbons, for instance the products sold by the company Total under the name Gemseal®, such as, in particular, the product Gemseal® 60 which is an isoparaffinic mixture derived from a totally hydrogenated petroleum fraction.

In the context of the preparation of a hydrocolloid mass according to the invention, use will preferably be made of a liquid plasticizer at a concentration comprised between about 10% and about 95% by weight relative to the total weight of the composition, and more preferably between about 30% and about 75% by weight relative to the total weight of the hydrocolloid mass.

In the context of the present description, the term "active substance" is intended to mean any substance that exerts a pharmacological activity, such as, in particular, bactericidal or bacteriostatic agents (chloramine, chlorhexidine, silver salts, zinc salts, metronidazole, penicillin, etc.), agents for promoting healing (hormones, peptides, etc.), enzymes for promoting wound cleaning (pepsin, trypsin, etc.), protease or metalloprotease inhibitors, painkillers or local anesthetics (lidocaine, cinchocaine) or nonsteroidal anti-inflammatory drugs (ibuprofen, ketoprofen, fenoprofen, diclofenac).

These active substances may be present in the dressing at concentrations ranging from 0.01% to 15% by weight, preferably from 3% to 8% by weight, it being possible for these concentrations to vary according to the active substance used.

The releasing properties of the copolymer used in the context of the present invention and also its properties on fibroblasts have been demonstrated in the examples given hereinafter. It has been noted that these properties are exerted at a low dose, i.e. when the dressing comprises from 0.1% to 20% by weight, preferably from 1% to 10% by weight, and more preferably approximately 5% by weight, of copolymer of a salt of 2-methyl-2-[(1-oxo-2-propenyl)amino]-1-propanesulfonic acid and of 2-hydroxyethylpropenoate ester.

DEMONSTRATION OF THE PROPERTIES OF THE COPOLYMER USED IN THE CONTEXT OF THE INVENTION a. Constituents Used The following constituents were used in order to prepare the various dressings of the present invention:

Sepinov EMT 10: a copolymer of a salt of 2-methyl-2-[(1-oxo-2-propenyl)amino]-1-propanesulfonic acid and of 2-hydroxyethylpropenoate ester, sold by the company SEPPIC.

Kraton G 1654 and G 1651: high-molecular-weight styrene-ethylene-butylene-styrene (S-EB-S) sold by the company Kraton.

Kraton D1111K: styrene-isoprene-styrene (SIS) copolymer containing at least 22% of polystyrene, sold by the company Kraton.

Ondina 917: a mineral oil sold by the company Shell.

Irganox 1010: pentaerythritol tetrakis(3-(3,5-di-tert-butyl-4-hydroxy-phenyl)propionate) sold by the company Ciba Specialty Chemicals.

Codex A petroleum jelly: petroleum jelly sold by the company Aiglon.

CMC Blanose 7H4XF: sodium carboxymethylcellulose sold by the company Hercules.

Luquasorb 1003: superabsorbent polymer of sodium polyacrylate, sold by BASF.

Silver sulfadiazine: sold by the company Argenol Bentley.

Potassium sucrose octasulfate: sold by the company Euticals.

b₁. Production of Elastomeric Masses

Examples 1 to 8

The elastomeric masses of Examples 1 to 8 were prepared by mixing in a Z-blade mixer. The setpoint temperature of Examples 3 and 4 was 140° C., that of Examples 1, 2 and 5 to 8 was 105° C.
1. The styrene-ethylenebutylene-styrene or styrene-isoprene-styrene triblock elastomers were mixed with half the mineral oil and with the antioxidant.
2. At 30 minutes, the petroleum jelly was added to the mixture.
3. At 40 minutes, the rest of the mineral oil was added.
4. At 55 minutes, the sodium carboxymethylcellulose or the superabsorbent polymer, as appropriate, the active substance, optionally the tackifying resin and, where appropriate, the Sepinov EMT 10 copolymer were added.

The mixer was emptied at 70 minutes.

Example 9

The elastomeric mass of Example 9 containing the Sepinov EMT 10 copolymer and potassium sucrose octasulfate (sold by the company Euticals) as active substance was prepared by mixing in a Z-blade mixer at a setpoint temperature of 110° C. according to the following process:
1. The petroleum jelly (codex A petroleum jelly sold by the company Aiglon) and the mineral oil (Ondina 917 sold by the company Shell) were mixed at a temperature of 89° C.
2. At 7 minutes, the copolymer was added.
3. At 12 minutes, the sodium carboxymethylcellulose (CMC Blanose 7H4XF sold by the company Hercules) and the active substance were added.
4. At 20 minutes, the high-molecular-weight S-EB-S (Kraton G 1654 sold by the company Kraton) and the antioxidant (Irganox 1010 sold by the company Ciba Specialty Chemicals) were added. The temperature of the mixture was then 106° C.
5. At 60 minutes, the tackifying resin (Escorez 5380 sold by the company Exxon Mobil Chemical) was added.

The mixer was emptied at 80 minutes.

Example 10

The elastomeric mass of example 10 containing potassium sucrose octasulfate (sold by the company Euticals) as active substance was prepared by mixing in a Z-blade mixer at a setpoint temperature of 110° C. according to the following process:
1. The petroleum jelly (codex A petroleum jelly sold by the company Aiglon) and the mineral oil (Ondina 917 sold by the company Shell) were mixed at a temperature of 89° C.
2. At 3 minutes, the sodium carboxymethylcellulose (CMC Blanose 7H4XF sold by the company Hercules) and the active substance were added.
3. At 10 minutes, the high-molecular-weight S-EB-S (Kraton G 1654 sold by the company Kraton) and the antioxidant (Irganox 1010 sold by the company Ciba Specialty Chemicals) were added. The temperature of the mixture was then 104° C.
4. At 40 minutes, the tackifying resin (Escorez 5380 sold by the company Exxon Mobil Chemical) was added.

The mixer was emptied at 55 minutes.

Example 11

The elastomeric mass of example 11 containing the Sepinov EMT 10 copolymer and silver sulfadiazine (sold by the company Argenol Bentley) as active substance was prepared by mixing in a Z-blade mixer at a setpoint temperature of 130° C. according to the following process:
1. The Sepinov EMT 10 copolymer and the mineral oil (Ondina 917 sold by the company Shell) were mixed at a temperature of 110° C.
2. At 5 minutes, the sodium carboxymethylcellulose (CMC Blanose 7H4XF sold by the company Hercules), the active substance and the petroleum jelly (codex A petroleum jelly sold by the company Aiglon) were added.
3. At 12 minutes, the high-molecular-weight S-EB-S (Kraton G 1651 sold by the company Kraton) and the antioxidant (Irganox 1010 sold by the company Ciba Specialty Chemicals) were added. The temperature of the mixture was then 106° C.
4. At 55 minutes, the tackifying resin (Escorez 5380 sold by the company Exxon Mobil Chemical) was added.

The mixer was emptied at 70 minutes.

Example 12

The elastomeric mass of example 12 containing silver sulfadiazine (sold by the company Argenol Bentley) as active substance was prepared by mixing in a Z-blade mixer at a setpoint temperature of 130° C. according to the following process:
1. The mineral oil (Ondina 917 sold by the company Shell), the sodium carboxymethylcellulose (CMC Blanose 7H4XF sold by the company Hercules) and the active substance were mixed at a temperature of 92° C.
2. At 2 minutes, the petroleum jelly (codex A petroleum jelly sold by the company Aiglon) was added.
3. At 7 minutes, the high-molecular-weight S-EB-S (Kraton G 1651 sold by the company Kraton) and the antioxidant (Irganox 1010 sold by the company Ciba Specialty Chemicals) were added. The temperature of the mixture was then 113° C.
4. At 41 minutes, the tackifying resin (Escorez 5380 sold by the company Exxon Mobil Chemical) was added.

The mixer was emptied at 60 minutes.

The amounts (expressed as weight per 100 grams) of the various constituents of the elastomeric masses thus prepared are given in table 1.

b₂. Production of Petroleum Jelly-Based Masses

Examples 13 to 18

The petroleum jelly-based masses of examples 13 to 18 were prepared at 45° C. in a beaker according to the following process:

The petroleum jelly (codex A petroleum jelly sold by the company Aiglon), the active substance (potassium sucrose octasulfate sold by the company Euticals or silver sulfadiazine from the company Argenol Bentley), as appropriate, the carboxymethylcellulose (CMC Blanose 7H4XF from the company Hercules) and, as appropriate, the copolymer (Sepinov EMT 10 sold by the company SEPPIC) were mixed manually.

The amounts (expressed as weight per 100 grams) of the various constituents of these masses are given in table 2.

TABLE 1

| | Ondina 917 | Kraton G 1651 | Kraton G 1654 | Kraton D 1111K | Irganox 1010 | Codex A petroleum jelly | CMC Blanose 7H4XF | Luquasorb 1003 | Escorez 5380 | Potassium sucrose octasulfate | Silver sulfadiazine | Sepinov EMT10 |
|---|---|---|---|---|---|---|---|---|---|---|---|---|
| Ex. 1 | 62.38 | | 6 | | 0.12 | 5 | 14 | | | 7.5 | | 5 |
| Ex. 2 | 67.38 | | 6 | | 0.12 | 5 | 14 | | | 7.5 | | |
| Ex. 3 | 71.2 | 4.93 | | | 0.12 | 5 | 10 | | | | 3.75 | 5 |
| Ex. 4 | 76.2 | 4.93 | | | 0.12 | 5 | 10 | | | | 3.75 | |
| Ex. 5 | 62.4 | | 6 | | 0.1 | 5 | | 14 | | 7.5 | | 5 |
| Ex. 6 | 67.4 | | 6 | | 0.1 | 5 | | 14 | | 7.5 | | |
| Ex. 7 | 38.4 | | | 10 | 0.1 | 5 | | 14 | 20 | 7.5 | | 5 |
| Ex. 8 | 43.4 | | | 10 | 0.1 | 5 | | 14 | 20 | 7.5 | | |
| Ex. 9 | 27.38 | | 6 | | 0.12 | 5 | 14 | | 35 | 7.5 | | 5 |
| Ex. 10 | 32.38 | | 6 | | 0.12 | 5 | 14 | | 35 | 7.5 | | |
| Ex. 11 | 36.2 | 4.93 | | | 0.12 | 5 | 10 | | 35 | | 3.75 | 5 |
| Ex. 12 | 41.2 | 4.93 | | | 0.12 | 5 | 10 | | 35 | | 3.75 | |

TABLE 2

| | Codex A petroleum jelly | CMC Blanose 7H4XF | Potassium sucrose octasulfate | Silver sulfadiazine | Sepinov EMT 10 |
|---|---|---|---|---|---|
| Example 13 | 78 | 9.5 | 7.5 | | 5 |
| Example 14 | 83 | 9.5 | 7.5 | | |
| Example 15 | 82.5 | | 7.5 | | 10 |
| Example 16 | 92.5 | | 7.5 | | |
| Example 17 | 86.25 | | | 3.75 | 10 |
| Example 18 | 96.25 | | | 3.75 | | c. Production of Dressings and Tested Products $c_1$. Interface dressings constituted of a mesh coated with an elastomeric mass were produced using the abovementioned elastomeric masses of examples 1 to 4.

More specifically, a mesh formed from a thermoset marquisette made of polyester (polyethylene terephthalate) yarns of 33 decitex in the warp and weft directions, having square mesh cells with an aperture of approximately 0.8 to 1 mm² (mesh 555 sold by the company MDB Texinov) was used here.

This mesh was coated with a layer of molten elastomeric mass at 135-145° C., and then the excess was removed by passing between two fixed rollers having a gap of 200 µm therebetween. The strip thus obtained was cut and then complexed with a 23 µm thick protective polyester film, on each of its sides, thus forming individual dressings packaged in impermeable pouches and sterilized under β-radiation at 25 kGy.

$c_2$. Sheets of elastomeric masses of examples 5 to 12 were prepared between two 75 µm sheets of siliconized polyester, by means of a heating press, the two plates of which were set at 95° C. The thickness of these sheets of elastomeric mass was calibrated by means of inserts having a thickness of 1150 µm, so as to obtain sheets of, on average, 1 mm.

$c_3$. The petroleum jelly-based masses of examples 13 to 18 was partly coated onto a viscose 552 mesh (sold by the company MDB Texinov) and partly conserved in order to analyze the release of the active substance contained in this mass.

$c_4$. The interface dressings prepared using the elastomeric masses of examples 1 to 4 were heat-complexed with a 4.5 mm thick hydrophilic polyurethane foam, sold by the company Corpura B.V under the trade name Vivo MFC.03. The complex was placed between two hotplates under pressure at a temperature of approximately 100° C. A polyester fingerlift having a thickness of 50 µm was applied to the side of the interface dressing. The complex dressings thus obtained were packaged individually in impermeable pouches and sterilized under β-radiation at 25 kGy.

The dressings thus obtained are hereinafter denoted "examples 19 to 22" and are represented in table 3.

TABLE 3

| Example 19 | Dressing of example 1 + polyurethane foam |
|---|---|
| Example 20 | Dressing of example 2 + polyurethane foam |
| Example 21 | Dressing of example 3 + polyurethane foam |
| Example 22 | Dressing of example 4 + polyurethane foam |

Method of Measuring the Release of an Active Substance

The ability of a copolymer of a salt of 2-methyl-2-[(1-oxo-2-propenyl)amino]-1-propanesulfonic acid and of 2-hydroxyethylpropenoate ester to promote the release of an active substance is illustrated by means of the following analysis methods:

In the case of interface dressings, prepared from the masses of examples 1 to 4 and 13 to 18, samples of 25 cm² of dressing (cut with a calibrated punch and precisely weighed) were introduced into an Erlenmeyer flask containing 10 ml of physiological saline solution. The glassware, hermetically sealed, was placed in an incubator at 37° C. for 24 h. The supernatant was removed and filtered. The amount of active substance was assayed by HPLC (high performance liquid chromatography) according to the methods described below.

In the case of the interface dressings complexed with a foam, of examples 19 to 22, the liquid was completely absorbed by the device. In this case, the dressing was saturated with physiological saline solution in order to obtain approximately 10 ml of supernatant.

In order to standardize the method, samples of 25 cm² of absorbent dressing (cut with a calibrated punch and precisely weighed) were placed in an Erlenmeyer flask containing 25 ml of physiological saline solution. The glassware, hermetically sealed, was placed in an incubator at 37° C. for 24 h. The supernatant was removed and the amount of active substance was assayed by HPLC (high performance liquid chromatography) according to the methods described below.

In the case of the masses in the form of sheets, of examples 5 to 12, samples of 25 cm² of sheet (cut with a calibrated punch and precisely weighed) were placed in an Erlenmeyer flask containing 10 ml of physiological saline solution. The glassware, sealed hermetically, was placed in an incubator at 37° C. for 24 h. The supernatant was removed and filtered. The amount of active substance was assayed by HPLC (high performance liquid chromatography) according to the methods described below.

In the case of the masses in the form of a paste/ointment, obtained using the masses of examples 13 to 18, 1000 mg of mass were spread out at the bottom of an Erlenmeyer flask containing 10 ml of physiological saline solution. The glassware, hermetically sealed, was placed in an incubator at 37° C. for 24 h. The supernatant was removed and filtered. The amount of active substance was assayed by HPLC (high performance liquid chromatography) according to the methods described below.

Method for Assaying Potassium Sucrose Octasulfate

The following conditions for assaying by high performance liquid chromatography (HPLC) were used:

Reagents
    Ammonium sulfate, for example Normapur code 21 333 296 from Prolabo.
    HPLC-grade demineralized water.
    Potassium sucrose octasulfate.
    Orthophosphoric acid, for example Carlo Erba code 406002 or equivalent.

Chromatographic Conditions
    Waters Alliance 2695 HPLC.
    $NH_2$ column.
    Eluent: aqueous solution of ammonium sulfate buffered at pH=3.00.
    Flow rate: 1 ml/min.
    Injected volume: 50 µl.
    Column temperature=30° C.
    Detection: refractometry (T int=35° C.).

Preparation of the Standard Solutions for the Chromatographic Analysis

A calibration range was prepared with 3 controls: 0.3 mg/ml-1 mg/ml-2.5 mg/ml.

The detection threshold for the potassium sucrose octasulfate was 0.06 mg/ml. When no peak was detected, the result was increased by the detection threshold.

Method for Assaying Silver Sulfadiazine

The silver sulfadiazine was assayed by high performance liquid chromatography (HPLC), under the following conditions:

Reagents
    HPLC-grade water.
    Orthophosphoric acid, for example Carlo Erba code 406002 or equivalent quality.
    Acetonitrile
    Silver sulfadiazine.

Chromatographic Conditions
    Flow rate: 1 ml/min.
    Column oven temperature: 30° C.
    Wavelength λ: 264 nm.
    Eluent phase: water/acetonitrile/orthophosphoric acid (respective volumes: 900/99/1).

Preparation of the Standard Solutions for the Chromatographic Analysis

A calibration range was prepared with 2 controls: 0.4 mg/ml-2.5 mg/ml.

The detection threshold for the silver sulfadiazine was 0.0006 mg/ml. When no peak was detected, the result was increased by the detection threshold.

Assaying Method: Results Determination

A calibration straight line was plotted using the calibration points, and the equation of the straight line $y=ax+b$ ($r^2>0.999$), in which y=surface area under the peak
x=concentration of the standard (in mg/ml)
$r^2$=determination coefficient,
was calculated.

The content of potassium sucrose octasulfate or silver sulfadiazine (x) was calculated.

The HPLC results are expressed in mg/ml.

The percentage of release of the active substance is calculated according to the following formula:

$$\text{Content}_\% = \frac{x \cdot V}{m \cdot C}$$

in which:

content %=release of the active substance relative to the theoretical content in the dressing.

X=release of active substance in the physiological saline solution in mg/ml (HPLC datum).

V: volume of physiological saline solution introduced during the release study (10 ml or 20 ml for the absorbent dressings).

m=mass of the coating (mg).

C=active principle content of the coating (%).

The results of the release measurements thus obtained are given in tables 4 to 7.

TABLE 4

Release of the active substance in the interface dressings of examples 1 to 4

| | Example 1 | Example 2 | Example 3 | Example 4 |
|---|---|---|---|---|
| Release of the active substance (mg/ml) | 0.74 | 0.06 | 0.155 | 0.007 |
| Release of the active substance (%) | 28.40 | 2.63 | 13.5 | 0.65 |

TABLE 5

Release of the active substance in sheets of elastomeric masses

| | Ex. 5 | Ex. 6 | Ex. 7 | Ex. 8 | Ex. 9 | Ex. 10 | Ex. 11 | Ex. 12 |
|---|---|---|---|---|---|---|---|---|
| Release of the active substance (mg/ml) | 0.77 | 0.06 | 1.10 | 0.06 | 1.98 | 0.06 | 0.085 | 0.003 |
| Release of the active substance (%) | 15.38 | 1.21 | 19.56 | 1.14 | 10.07 | 0.31 | 0.91 | 0.03 |

TABLE 6

Release of the active substance in the interface dressings of examples 13 to 18

| | Ex. 13 | Ex. 14 | Ex. 15 | Ex. 16 | Ex. 17 | Ex. 18 |
|---|---|---|---|---|---|---|
| Release of the active substance (mg/ml) | 3.01 | 1.16 | 6.02 | 0.32 | 0.393 | 0.098 |
| Release of the active substance (%) | 63.74 | 18.09 | 87.73 | 5.04 | 12.78 | 3.15 |

TABLE 7

Release of the active substance in the interface dressings complexed with foams, of examples 19 to 22

|  | Ex. 19 | Ex. 20 | Ex. 21 | Ex. 22 |
|---|---|---|---|---|
| Release of the active substance (mg/ml) | 0.53 | 0.09 | 0.10 | 0.006 |
| Release of the active substance (%) | 50 | 9.89 | 17.97 | 1.02 |

These results show that, although it is not a surfactant, such as polysorbate 80 (Montanox 80, sold by the company SEPPIC), a copolymer of a salt of 2-methyl-2-[(1-oxo-2-propenyl)amino]-1-propanesulfonic acid and of 2-hydroxyethylpropenoate ester allows release of the active substance. These results also show that, whatever the nature of the active substance (water-soluble or water-insoluble) is, the release nevertheless takes place.

Comparative Study

The ability of the abovementioned copolymer to release an active substance (such as potassium sucrose octasulfate or silver sulfadiazine) was measured in masses comprising at least one fatty substance, and compared with that obtained with a surfactant, in the case in point polysorbate 80 (Montanox 80 sold by the company SEPPIC).

To this effect, elastomeric masses containing polysorbate 80 and an active substance (the potassium sucrose octasulfate sold by the company Euticals) were prepared according to the same process as for examples 1 to 8, other than the fact that the Sepinov EMT 10 copolymer was replaced with Montanox 80 sold by the company SEPPIC.

The amounts (expressed by weight per 100 grams) of the various constituents of the masses thus prepared (examples 23 and 24) are given in table 8.

Interface dressings constituted of a mesh coated with an elastomeric mass were produced using the masses thus prepared.

More specifically, a mesh formed from a thermoset marquisette made of polyester (polyethylene terephthalate) yarns of 33 decitex in the warp and weft directions, having square mesh cells with an aperture of approximately 0.8 to 1 mm$^2$ (mesh 555 sold by the company MDB Texinov) was used here.

This mesh was coated with a layer of molten mass at 115° C., and then the excess was removed by passing between two fixed rollers having a gap of 200 μm therebetween. The strip thus obtained was cut and then complexed with a protective polyester film 23 μm thick, on each of its sides, thus forming individual dressings packaged in impermeable pouches and sterilized under β-radiation at 25 kGy.

Comparison of the Ability to Release an Active Substance Between the Copolymer Used According to the Invention and a Surfactant of Polysorbate 80 Type The dressings of examples 1 and 3 (containing the Sepinov EMT 10 copolymer as releasing agent) and the dressings of examples 23 and 24 (containing Montanox 80 as releasing agent) were tested according to the method of measuring the release of an active substance from interface dressings described above.

The results obtained are given in table 9.

TABLE 9

Release of an active substance (expressed as mg/ml and as percentage) using the masses according to examples 1, 23, 3 and 24

|  | Example 1 | Example 23 | Example 3 | Example 24 |
|---|---|---|---|---|
| Release of the active substance (mg/ml) | 0.74 | 0.87 | 0.155 | 0.251 |
| Release of the active substance (%) | 28.4 | 32.94 | 13.5 | 19.6 |

As it can be seen, substantially the same release of the active substance is obtained, irrespective of its nature, with the Montanox® 80 or the Sepinov EMT 10 copolymer.

Demonstration of the Absence of Cytotoxicity with Respect to Fibroblasts of the Copolymer Used in the Context of the Invention In order to demonstrate this advantageous property, interface dressings were tested on fibroblast cultures according to the following method:

Materials and Methods

Cells Used:

Type: pool of normal human dermal fibroblasts (NHDF) R9PF2

Culture: 37° C., 5% $CO_2$

Culture Medium:
  DMEM (Dulbecco's Modified Eagle Medium, Invitrogen 21969035)
  2 mM L-glutamine (Invitrogen 25030024)
  50 UI/ml penicillin, 50 μg/ml streptomycin (Invitrogen 15070063)
  10% fetal calf serum (v/v, Invitrogen 10270098).

Products Tested:
  Dressings according to examples 1 and 23 were cut to the size of the wells and tested.

Effects on Proliferation:
  The fibroblasts were seeded at confluence in a 12-well plate.
  Pieces of each dressing were cut to a size of 1.4 cm×1.4 cm (i.e. 1.96 cm$^2$), applied to the surface of the fibroblasts and held in place using a plug. A control without dressing but with a plug, and also a control without dressing and without plug were carried out.

TABLE 8

|  | Ondina 917 | Kraton G 1654 | Irganox 1010 | Vaseline Codex A | CMC Blanose 7H4XF | Potassium sucrose octasulfate | Silver sulfadiazine | Montanox 80 |
|---|---|---|---|---|---|---|---|---|
| Example 23 | 62.38 | 6 | 0.12 | 5 | 14 | 7.5 |  | 5 |
| Example 24 | 71.2 | 4.93 | 0.12 | 5 | 10 |  | 3.75 | 5 |

The cells were then incubated for 48 hours, 96 hours and 168 hours (7 days) at 37° C. and 5% $CO_2$. For each incubation time, the metabolic activity was measured using a standard MTT test, which accounts for the mitochondrial dehydrogenases activity. Tritiated thymidine ([methyl-3H]-thymidine, Amersham TRK 686 2.5 μCi/ml final concentration) was added during the last 24 hours of incubation, and then the DNA of the cells of the cell layers was extracted and purified and the radioactivity incorporated into the DNA was counted using a scintillation counter.

All experiments were carried out in triplicate. The raw counting data were transferred and processed using the Prism® software (Graph Pad Software).

The results obtained are expressed in counts per minute (cpm), and then as percentage relative to the control, according to the following formula:

$$\%_{control} = (cpm_{test}/cpm_{control}) \times 100$$

in which:

$cpm_{test}$: number of counts per minute obtained with the test
$cpm_{control}$ number of counts per minute obtained with the control.

The results obtained are given in table 10.

Photographs of the fibroblasts were taken at the end of the treatment after staining with MTT. These photographs are reproduced in FIG. 1.

TABLE 10

Fibroblast viability (expressed as percentage) 48 h, 96 h, and 168 h after treatment

| | Fibroblast viability at 48 hours (%) | Fibroblast viability at 96 hours (%) | Fibroblast viability at 168 hours (%) |
|---|---|---|---|
| Control | 100 | 100 | 100 |
| Control without plug | 98 | 103 | 107 |
| Dressing according to example 1 | 128 | 140 | 140 |
| Dressing according to example 23 | 70 | 68 | 57 |

As shown from the results of table 10, the use of the Sepinov EMT 10 copolymer in dressings, in amounts equivalent to a surfactant such as Montanox 80, makes it possible to release an active substance in equivalent proportions and exhibits a further advantage, which is that of promoting fibroblast proliferation.

FIG. 1 shows the effect of the dressings of examples 1 and 23 on cell viability after direct contact with the fibroblasts after 48 h, 96 h and 168 h. This observation of the morphology of the fibroblasts after removal of the dressings and staining with MTT was visualized by optical microscopy and the taking of representative photographs (×10 objective) and confirms the beneficial effect of the Sepinov EMT 10 copolymer on fibroblast proliferation in comparison with Montanox 80.

The invention claimed is:

1. A dressing comprising a mass, wherein the mass comprises a hydrocolloid in an amount of between 2 and 20% by weight of the mass, at least one selected from the group consisting of a fatty substance and an elastomeric matrix, at least one active substance, and a copolymer of a salt of 2-methyl-2-[(1-oxo-2-propenyl)amino]-1-propanesulfonic acid and of 2-hydroxyethylpropenoate ester,
wherein the copolymer is included in an amount sufficient for increasing an amount of the active substance that is released from the dressing as compared to that of a corresponding dressing that does not comprise the copolymer,
wherein the amount of the copolymer included in the dressing is between 1% to 20% by weight, and
wherein the amount of the active substance included in the dressing is between 0.01% and 15% by weight.

2. The dressing as claimed in claim 1, wherein the salt of 2-methyl-2-[(1-oxo-2-propenyl)amino]-1-propanesulfonic acid is a sodium salt.

3. The dressing as claimed in claim 1, wherein said active substance is selected from the group consisting of bactericidal agents, bacteriostatic agents, agents for promoting healing, enzymes for promoting wound cleaning, protease inhibitors, metalloprotease inhibitors, painkillers, local anesthetics and nonsteroidal anti-inflammatory drugs.

4. The dressing as claimed in claim 1, which comprises between 1% and 10% by weight of said copolymer.

5. The dressing as claimed in claim 1, which comprises between 3% and 8% by weight of said active substance.

6. A method for releasing an active substance from a dressing composition that comprises a mass, wherein the mass comprises a hydrocolloid in an amount of between 2 and 20% by weight of the mass and, at least one selected from the group consisting of a fatty substance and an elastomeric matrix and at least one active substance, the method comprising incorporating a copolymer of a salt of 2-methyl-2-[(1-oxo-2-propenyl)amino]-1-propanesulfonic acid and of 2-hydroxyethylpropenoate ester in said dressing composition in an amount sufficient for increasing an amount of the active substance that is released from the dressing as compared to that of a corresponding dressing that does not comprise the copolymer,
wherein the amount of the copolymer incorporated in the dressing is between 1% to 20% by weight, and
wherein the amount of the active substance included in the dressing is between 0.01% and 15% by weight.

7. The method as claimed in claim 6, wherein said salt of 2-methyl-2-[(1-oxo-2-propenyl)amino]-1-propanesulfonic acid is a sodium salt.

8. The method as claimed in claim 6, wherein said active substance is selected from the group consisting of bactericidal agents, bacteriostatic agents, agents for promoting healing, enzymes for promoting wound cleaning, protease inhibitors, metalloprotease inhibitors, painkillers, local anesthetics and nonsteroidal anti-inflammatory drugs.

9. The method as claimed in claim 6, wherein the composition comprises an elastomeric matrix.

10. The dressing as claimed in claim 3, wherein said active substance is a bactericidal or bacteriostatic agent.

11. The dressing as claimed in claim 10, wherein said active substance is selected from the group consisting of: chloramine, chlorhexidine, silver salts, zinc salts, metronidazole and penicillin.

12. The dressing as claimed in claim 11, wherein said active substance is silver salts or zinc salts.

13. The dressing as claimed in claim 12, wherein said active substance is silver salts.

14. The dressing as claimed in claim 3, wherein said active substance is an agent for promoting healing.

15. The dressing as claimed in claim 14, wherein said active substance is potassium sucrose octasulfate.

16. The dressing as claimed in claim 3, wherein said active substance is a painkiller or local anesthetic.

17. The dressing as claimed in claim 16, wherein said active substance is lidocaine or cinchocaine.

18. The dressing as claimed in claim 3, wherein said active substance is a nonsteroidal anti-inflammatory drug.

19. The dressing as claimed in claim 18, wherein said active substance is selected from the group consisting of: ibuprofen, ketoprofen, fenoprofen, and diclofenac.

20. The dressing as claimed in claim 1, wherein the hydrocolloid is at least one selected from the group consisting of pectin, alginate, a natural plant gum, a cellulose derivative or an alkali metal salt thereof, and a superabsorbent.

21. The dressing as claimed in claim 1, wherein the hydrocolloid is a carboxymethylcellulose or a sodium or calcium salt thereof.

22. The dressing as claimed in claim 21, wherein the fatty substance is a paraffin oil, petroleum jelly, or a mineral oil formed from compounds of paraffinic, naphthenic or aromatic nature.

23. The dressing as claimed in claim 22, wherein the active agent is a bacteriostatic silver salt, potassium sucrose octasulfate, lidocaine, cinchocaine, or a non-steroidal anti-inflammatory drug.

\* \* \* \* \*